US006565884B2

(12) United States Patent
Nimni

(10) Patent No.: US 6,565,884 B2
(45) Date of Patent: May 20, 2003

(54) BONE GRAFT MATERIAL INCORPORATING DEMINERALIZED BONE MATRIX AND LIPIDS

(75) Inventor: Marcel E. Nimni, Santa Monica, CA (US)

(73) Assignee: Interpore Cross International, Irvine, CA (US)

(*) Notice: Subject to any disclaimer, the term of this patent is extended or adjusted under 35 U.S.C. 154(b) by 0 days.

(21) Appl. No.: 09/950,264

(22) Filed: Sep. 10, 2001

(65) Prior Publication Data

US 2003/0049326 A1 Mar. 13, 2003

(51) Int. Cl.⁷ .......................... A61K 9/14; A61K 35/32; A61F 13/00; A61F 2/00
(52) U.S. Cl. ...................... 424/484; 424/422; 424/423; 424/549
(58) Field of Search ................................. 424/484, 423, 424/318, 422, 549; 530/350; 514/560, 558

(56) References Cited

U.S. PATENT DOCUMENTS

| 4,191,747 A | | 3/1980 | Scheicher |
| 4,196,218 A | * | 4/1980 | Thiele .................. 424/318 |
| 4,394,370 A | | 7/1983 | Jefferies |
| 4,472,840 A | | 9/1984 | Jefferies |
| 4,642,120 A | | 2/1987 | Nevo et al. |
| 4,795,804 A | * | 1/1989 | Urist .................... 530/350 |
| 4,801,299 A | | 1/1989 | Brendel et al. |
| 4,879,135 A | | 11/1989 | Greco et al. |
| 4,946,792 A | | 8/1990 | O'Leary |
| 4,976,733 A | | 12/1990 | Girardot |
| 5,053,049 A | | 10/1991 | Campbell |
| 5,067,962 A | | 11/1991 | Campbell et al. |
| 5,073,373 A | | 12/1991 | O'Leary et al. |
| 5,229,497 A | | 7/1993 | Boni |
| 5,236,456 A | | 8/1993 | O'Leary et al. |
| 5,284,655 A | | 2/1994 | Bogdansky et al. |
| 5,290,558 A | * | 3/1994 | O'Leary et al. ............ 424/422 |

(List continued on next page.)

OTHER PUBLICATIONS

J.T. Irving & R.E. Wuthier, "Histochemistry and Biochemistry of Calcification with Special Reference to the Role of Lipids," *Clin. Orthoped. Rel. Res.* 56:237–260 (1968).
M.R. Urist et al., "Lipids Closely Associated with Bone Morphogenetic Protein (BMP) . . . and Induced Heterotopic Bone Formation," *Connect. Tissue Res.* 36: 9–20 (1997).
M.E. Nimni, "Polypeptide Growth Factors: Targeted Delivery Systems," *Biomaterials* 18: 1201–1225 (1997).
M.R. Urist & T.A. Dowell, "The Inductive Substratum for Osteogenesis in Pellets of Particulate Bone Matrix," *Cli Orthoped. Rel. Res.* 61:61–68 (1969).

(List continued on next page.)

Primary Examiner—Thurman K. Page
Assistant Examiner—Blessing Fubara
(74) Attorney, Agent, or Firm—Christie, Parker & Hale, LLP

(57) ABSTRACT

A demineralized bone putty composition comprises: (1) demineralized bone matrix (DBM); and (2) a lipid fraction selected from the group consisting of lecithin and a mixture of lecithin and triglycerides containing unsaturated fatty acids. The putty composition is moldable, biocompatible, slowly resorbable, and soluble in tissue fluids, and non-extrudable. The composition delivers a biologically active product to animals and humans that will enhance bone formation at sites where bone is lost, deficient, or present in suboptimal amounts. The composition can further comprise calcium, an antioxidant such as Vitamin E or Vitamin C, or a hydrophilic polymer such as methylcellulose or hydroxypropyl methylcellulose.

41 Claims, 2 Drawing Sheets

Subcutaneous implantation

U.S. PATENT DOCUMENTS

| | | |
|---|---|---|
| 5,298,254 A | 3/1994 | Prewett et al. |
| 5,314,476 A | 5/1994 | Prewett et al. |
| 5,405,390 A | 4/1995 | O'Leary et al. |
| 5,439,684 A | 8/1995 | Prewett et al. |
| 5,484,601 A | 1/1996 | O'Leary et al. |
| 5,510,396 A | 4/1996 | Prewett et al. |
| 5,607,476 A | 3/1997 | Prewett et al. |
| 5,707,962 A | 1/1998 | Chen et al. |
| 5,980,948 A | 11/1999 | Goedemoed et al. |
| 6,123,731 A | 9/2000 | Boyce et al. |

OTHER PUBLICATIONS

M.R. Urist & B.S. Strates, "Bone Morphogenetic Protein," *J. Dent. Res.* 50:1392–1406 (1971).

B.S. Strates & J.J. Tideman, "Contribution of Osteoinductive and Osteoconductive Properties of Demineralized Bone Matrix to Skeletal Repair," *Euro. J. Exp. Musculoskel. Res.* 2:61–67 (1993).

M.R. Urist et al., "Solubilized and Insolubilized Bone Morphogenetic Protein," *Proc. Natl. Acad. Sci. USA* 76:1828–1832 (1979).

C.B. Huggins et al., "Transformation of Fibroblasts by Allogeneic and Xenogeneic Transplants of Demineralized Tooth and Bone," *J. Exp. Med.* 132:1250–1258 (1970).

A.H. Reddi & C.B. Huggins, "Influence of Transplanted Tooth and Bone on Transformation of Fibroblasts," *Proc. Soc. Exp. Biol. Med.* 143:634–637 (1973).

G.D. Syftestad & M.R. Urist, "Degradation of Bone Matrix Morphogenetic Activity by Pulverization," *Clin. Orthoped. Rel. Res.* 141:281–286 (1979).

M.R. Urist, "The Search for and the Discovery of Bone Morphogenetic Protein (BMP)," *In Bone Grafts, Derivatives, and Substitutes* (M.R. Urist, B.T. O'Conner & R.G. Burwell, eds., Butterworth Heineman, London, 1994), pp. 315–362.

M. Muthukumaran et al., "Dose–Dependence of and Threshold for Optimal Bone Induction by Collagenous Bone Matrix and Osteogenin–Enriched Fraction," *Col. Rel. Res.* 8:433–441 (1988).

R.G. Hammonds, Jr. et al, "Bone–Inducing Activity of Mature BMP–2b Produced from a Hybrid BMP–2a/2b Precursor," *Mol. Endocrinol.* 5:149–155 (1991).

U. Ripamonti et al., "The Critical Role of Geometry of Porous Hydroxyapatite Delivery System in Induction of Bone by Osteogenin, a Bone Morphogenetic Protein," *Matrix* 12:202–212 (1992).

U. Ripamonti et al., "Induction of Bone in Composites of Osteogenin and Porous Hydroxyapatite in Baboons," *Plast. Reconstr. Surg.* 89:731–739 (1992).

M.R. Urist et al., "Neutral Lipids Facilitate Transfer of Bone Morphogenetic Proteins and Other Noncollagenous Proteins," *Med. Hypotheses* 49: 465–475 (1997).

M.R. Urist, "Bone Formation by Autoinduction," *Science* 150: 893 (1965).

E. Maddox et al., "Optimizing Human Demineralized Bone Matrix for Clinical Application," *Tissue Engineer.* 6:441–448 (2000).

R.R. Wuthier & E.D. Eanes, "Effect of Phospholipids on the Transformation of Amorphous Calcium Phosphate to Hydroxyapatite in Vitro," *Calcif. Tissue Res.* 19: 197–210 (1975).

M.E. Nimni et al., "The Effect of Aging on Bone Formation in Rats: Biochemical and Histological Evidence for Decreased Bone Formation Capacity," *Calcif. Tissue Int.* 37: 617–624 (1985).

\* cited by examiner

BONE GRAFT MATERIAL INCORPORATING DEMINERALIZED BONE MATRIX AND LIPIDS

BACKGROUND OF THE INVENTION

1. Field of the Invention
2. General Background and State of the Art

This invention is directed to a bone graft material incorporating demineralized bone matrix and lipids for particular use in enhancing bone formation.

One of the few tissues that regenerates in mammals is bone. To a great extent, this is due to the ability of specific growth factors to stimulate stem cells along the chondrogenic and osteogenic pathways and the role of mechanical forces that encourage bone remodeling.

Significant efforts have been made to enhance bone healing using decalcified bone matrix as an inducer. Decalcified bone matrix, which is mostly collagen with small amounts of growth- and differentiation-inducing molecules, is able to stimulate bone formation, even after implantation (subcutaneously or intramuscularly) at ectopic sites where there is no bone. The chondro-osteogenic response induced by implants of demineralized rabbit (M. R. Urist & T. A. Dowell, "The Inductive Substratum for Osteogenesis in Pellets of Particulate Bone Matrix," Clin. Orthoped. Rel. Res. 61:61–68 (1969); M. R. Urist & B. S. Strates, "Bone Morphogenetic Protein," J. Dent. Res. 50:1392–1406 (1971)) and rat bone matrix (C. B. Huggins et al., "Transformation of Fibroblasts by Allogeneic and Xenogeneic Transplants of Demineralized Tooth arid Bone," J. Exp. Med. 132:1250–1258 (1970); A. H. Reddi & C. B. Huggins, "Influence of Transplanted Tooth and Bone on Transformation of Fibroblasts," Proc. Soc. Exp. Biol. Med. 143:634–637 (1973); G. D. Syftestad & M. R. Urist, "Degradation of Bone Matrix Morphogenetic Activity by Pulverization," Clin. Orthoped. Rel. Res. 141:281–286 (1979)).

The data suggested that bone morphogenetic protein was associated with a relatively acid-resistant, trypsin labile, water-insoluble non-collagenous protein of previously uncharacterized nature (B. S. Strates & J. J. Tideman, "Contribution of Osteoinductive and Osteoconductive Properties of Demineralized Bone Matrix to Skeletal Repair," Euro. J. Exp. Musculoskel. Res. 2:61–67 (1993); M. R. Urist et al., "Solubilized and Insolubilized Bone Morphogenetic Protein," Proc. Natl. Acad. Sci. USA 76:1828–1832 (1979). This has been followed by extensive work attempting to further purify factors with bone morphogenetic potential (M. R. Urist, "The Search for Discovery of Bone Morphogenetic Protein (BMP)," In Bone Grafts, Derivatives, and Substitutes (M. R. Urist, B. T. O'Conner & R. G. Burwell, eds., Butterworth Heineman, London, 1994), pp. 315–362), and subsequently to generate active recombinant molecules of human origin.

The most widely used carrier for BMPs, either as a mixture of the bioactive factor extracted directly from human or animal bones using procedures described in the literature or recombinant molecules of the most active individual species, is DBM (demineralized bone matrix) from cortical bone of various animal sources. It is purified by a variety of procedures for the removal of non-collagenous proteins and other antigenic determinants. It usually consists of more than 99% type I collagen. Essentially, one can look at this approach as one of restoring an otherwise inactive bone matrix to an active form, as previously described.

Acid (HCl)-demineralized bone matrix, which contains a mixture of BMPs, consistently induces formation of new bone with a quantity of powdered matrices in the 10–25 mg range, while less than 10 mg fails to induce bone formation. Addition of acid-soluble type I collagen and chondroitin-6-sulfate promoted bone yield. Bone matrix inactivated by extraction with guanidine hydrochloride, an efficient protein denaturant, restores bone-forming activity by the addition of partially purified BMP-3 or recombinant BMP-2. Thus, new bone formation requires a combination of BMP and an insoluble collagenous substratum that can include chondroitin-6-sulfate (M. Muthukumaran et al., "Dose-Dependence of and Threshold for Optimal Bone Induction by Collagenous Bone Matrix and Osteogenin-Enriched Fraction," Col. Rel. Res. 8:433–441 (1988); R. G. Hammonds, Jr. et al, "Bone-Inducing Activity of Mature BMP-2b Produced from a Hybrid BMP-2a/2b Precursor," Mol. Endocrinol. 5:149–155 (1991); U. Ripamonti et al., "The Critical Role of Geometry of Porous Hydroxyapatite Delivery System in Induction of Bone by Osteogenin, a Bone Morphogenetic Protein," Matrix 12:202–212 (1992); U. Ripamonti et al., "Induction of Bone in Composites of Osteogenin and Porous Hydroxyapatite in Baboons," Plast. Reconstr. Surg. 89:731–739 (1992)). The same preparation of partially purified bovine BMP-3 was inactive when implanted subcutaneously without an insoluble collagenous matrix, but when combined with collagen, induced bone formation.

Reconstituted collagen can sometimes be used as a carrier for BMPs with less predictable results. However, a fibrous form of purified telopeptide-free collagen, which is intrinsically less soluble and biodegradable than the reconstituted collagen, is an effective carrier material.

Lipids were found to be present in very large amounts at various sites of normal bone formation (J. T. Irving & R. E. Wuthier, "Histochemistry and Biochemistry of Calcification with Special Reference to the Role of Lipids," Clin. Orthoped. Rel. Res. 56:237–260 (1968). Although there have been suggestions that the incidence and quantity of bone formation are greatest when BMP is delivered combined with the tissue using various biological synthetic materials (M. R. Urist et al., "Lipids Associated Closely with Bone Morphogenetic Protein (BMP) and Induced Heterotopic Bone Formation," Connect. Tissue Res. 36:9–20 (1997)), there is still a need for improved carriers for optimal results. There has been no suggestion that lecithin would serve as a suitable carrier. In work reported by Urist and coworkers (M. R. Urist et al., "Neutral Lipids Facilitate Transfer of Bone Morphogenetic Proteins and Other Noncollagenous Proteins," Med. Hypotheses 49:465–475 (1997), composites of recombinant BMP-2 and acetone-soluble lipids were reported to induce larger deposits of bone than implants of recombinant BMP-2 without acetone soluble lipids. Acetone soluble lipids consisted chiefly of triglycerides, cholesterol, and saturated short chain fatty acids, and included little or no phospholipids.

There is particularly a need for an improved matrix for supplying the demineralized bone matrix that is easily moldable, biocompatible, slowly resorbable, and insoluble in tissue fluids. There is a particular need for the development of compositions that can be varied in their physical form and consistency so that they can be made more solid or more liquid as the need requires.

INVENTION SUMMARY

In general, a demineralized bone putty composition according to the present invention comprises:

(1) demineralized bone matrix (DBM); and
(2) a lipid fraction selected from the group consisting of lecithin and a mixture of lecithin and triglycerides containing unsaturated fatty acids.

The mixture is such that the putty composition is moldable, biocompatible, slowly resorbable, insoluble in tissue fluid, and non-extrudable.

Typically, the composition comprises about 30–40% of DBM and about 60% of the lipid fraction.

In one embodiment of the present invention, the lipid fraction comprises lecithin.

In another embodiment of the present invention, the lipid fraction comprises a mixture of lecithin and triglycerides containing unsaturated fatty acids. Typically, when the composition contains a mixture of lecithin and triglycerides, the mixture of lecithin and triglycerides containing unsaturated fatty acids is about a 1:1 mixture.

The composition can further comprise a long-chain saturated fatty acid such as palmitic acid.

The DBM can be human DBM, rat DBM, or DBM from another animal such as a cow, a horse, a pig, a dog, a cat, a sheep, or another socially or economically important animal species. In one preferred embodiment, the DBM is delipidated, such as by treatment with a chloroform-methanol mixture.

The composition can further comprise other ingredients. In one alternative, the composition can further comprise a calcium salt.

In another alternative, the composition can further comprise at least one antioxidant selected from the group consisting of Vitamin E and Vitamin C.

In still another alternative, the composition can further comprise an ingredient selected from the group consisting of methylcellulose and hydroxypropyl methylcellulose.

The lipid fraction of the composition can be sterilized by radiation using standard radiation sterilization techniques.

The composition can be formulated so that the phospholipids are solid or liquid at room temperature.

BRIEF DESCRIPTION OF THE DRAWINGS

The following invention will become better understood with reference to the specification, appended claims, and accompanying drawings, where:

DETAILED DESCRIPTION OF THE PREFERRED EMBODIMENTS

Figure 1:
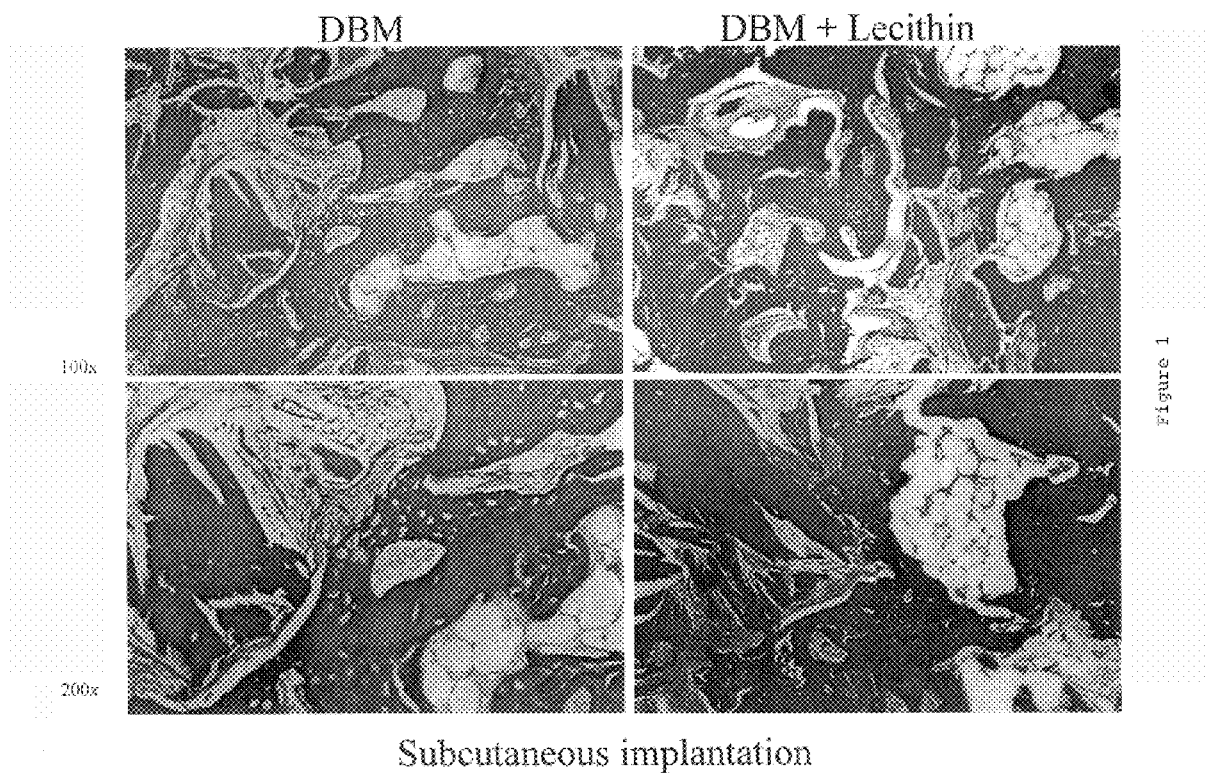
FIG. 1 is a photomicrograph that shows new bone formation in the DBM/composite after 28 days implantation: (a) subcutaneously; and (b) intramuscularly.

We have developed an improved demineralized bone putty composition that meets these needs. In general, a demineralized bone putty composition according to the present invention comprises:

(1) demineralized bone matrix (DBM); and
(2) a lipid fraction selected from the group consisting of lecithin and a mixture of lecithin and triglycerides containing unsaturated fatty acids.

The mixture is such that the putty composition is moldable, biocompatible, slowly resorbable, insoluble in tissue fluid, and non-extrudable.

The composition can comprise from about 20% to about 80% of DBM and from about 80% to about 20% of the lipid fraction. Typically, the composition comprises about 30–40% of DBM and about 60% of the lipid fraction. Preferably, the composition comprises from about 35% to about 40% of DBM. Percentages recited for the DBM and lipid fraction are weight percentages unless indicated otherwise. In preparation of compositions according to the present invention, the DBM and lipid fraction can actually be dispensed by volume as long as the resulting weight percentages are as specified.

The preparation of demineralized bone matrix (DBM) is well understood in the art and is described, for example, in M. E. Nimni, "Polypeptide Growth Factors: Targeted Delivery Systems," *Biomaterials* 10: 1201–1225 (1997), incorporated herein by this reference, and articles referenced therein. In general, DBM is prepared from cortical bone of various animal sources. It is purified by a variety of procedures for the removal of non-collagenous proteins and other antigenic determinants. It typically consists of more than 99% Type I collagen. The DBM can be, for example, human DBM or rat DBM; DBM from other species can alternatively be used. For example, the DBM can be DBM from another animal such as a cow, a horse, a pig, a dog, a cat, a sheep, or another socially or economically important animal species.

In one preferred embodiment, as described in Example 1, the DBM is delipidated, such as by treatment with a mixture of chloroform and methanol. A particularly preferred mixture of chloroform and methanol is a 1:1 mixture of chloroform and methanol. Other solvents can alternatively be used for delipidation.

In one embodiment of the present invention, the lipid fraction comprises lecithin.

In another embodiment of the present invention, the lipid fraction comprises a mixture of lecithin and triglycerides containing unsaturated fatty acids. Typically, when the composition contains a mixture of lecithin and triglycerides, the mixture of lecithin and triglycerides containing unsaturated fatty acids is about a 1:1 mixture.

Lecithin is also known as phosphatidyl choline. Preferably, the fatty acids in lecithin suitable for use in preparations according to the present invention have chain lengths of 16 to 18 carbon atoms. Less preferably, fatty acids having other chain lengths can be used. Additionally, other phospholipids such as phosphatidyl ethanolamine can be substituted for phosphatidyl choline. However, phosphatidyl choline (lecithin) is typically preferred. The use of lecithin enhances the osteoinductivity of DBM as well as providing better handling properties.

A particularly suitable source of unsaturated fatty acids is corn oil. However, other vegetable oils containing high proportions of unsaturated fatty acids can alternatively be used.

Corn oil comprises approximately 15% saturated fatty acids. The remainder, approximately 85% of the fatty acids, are unsaturated: 25% mono-unsaturated, mostly oleic acid; 59% di-unsaturated, mostly linoleic acid; about 1% of fatty acids with higher degrees of unsaturation, mostly linolenic acid.

As indicated below, the lipid portion can further contain long chain saturated fatty acids such as palmitic acid (hexadecanoic acid). Other long-chain fatty acids can be used in place of or in addition to palmitic acid.

The lipid portion of the preferred composition contains lecithin combined with mixed triglycerides present in corn oil. The relative proportions of the lecithin and the mixed triglycerides can be varied depending on the fluidity or other physical properties desired. For example, and without limitation, the proportions can be 20:80, 40:60, or 35:65. Other proportions can be used. For mixing with hydroxypropyl methylcellulose, 20:80 is preferred.

In another preferred embodiment, the lipid portion can comprise 25% of a lipid preparation that is designated 90G and 75% of a lipid preparation that is designated 53MCT. The lipid preparation that is designated 90G is more than 90% lecithin. The lipid preparation that is designated 53MCT is approximately 53% lecithin with the remainder being medium chain triglycerides.

Other lipid fractions can be used.

The composition can further comprise other ingredients. In one alternative, the composition can further comprise a calcium salt. The proportion of the calcium salt can be from about 0.1% to about 2%. More preferably, the proportion of the calcium salt is from about 0.5% to about 2%. The calcium salt can be $CaCO_3$ or $Ca_3(PO_4)_2$. However, other calcium salts can be used.

The composition can further comprise at least one antioxidant selected from the group consisting of Vitamin E and Vitamin C.

The antioxidant can be Vitamin E. A suitable Vitamin E is tocopherol, such as α-tocopherol. A suitable preparation of α-tocopherol is mixed isomers from natural sources. Vitamin E can comprise from about 0.01% to about 1.0% of the composition. Preferably, if present, Vitamin E comprises about 0.10% of the composition.

The antioxidant can be Vitamin C. A suitable preparation of Vitamin C is ascorbic acid or a long-chain fatty acid ester of ascorbic acid such as ascorbyl palmitate, ascorbyl stearate, or ascorbyl myristate. Vitamin C can comprise from about 0.01% to about 2% of the composition. Typically, if present, Vitamin C comprises from about 0.1% to about 0.5% of the composition. Preferably, if present, Vitamin C comprises about 0.2% of the composition.

The composition can further comprise an ingredient selected from the group consisting of methylcellulose and hydroxypropyl methylcellulose.

The lipid fraction of the composition can be sterilized by radiation using standard radiation sterilization techniques, such as gamma radiation or electron beam radiation.

The key ingredients for bone to form include the availability of a calcifiable matrix, called osteoid, and the subsequent deposition of calcium and phosphate ion in its interstices to form a rigid composite.

The growth factors described above stimulate the synthesis of such osteoid by cells that reside in the environment. The addition of phosphate in the form of lecithin and calcium in the form of calcium carbonate or other calcium salts provide the ingredients to enhance a mineralization of the previously formed osteoid. The resultant free phosphate ions, generated by endogenous alkaline phosphatases, and the solubilized forms of calcium, are then able to nucleate around the new collagen to generate the characteristic bone material, hydroxyapatite.

Both these ions, phosphate and calcium, are normally present at sites of calcification, where they are concentrated by specific biological processes. The vehicle-carrier used in this invention, at the same time that it provides a moldable vehicle for delivery, provides additional amounts of those ingredients necessary for bones to form.

Lecithin (phosphatidyl choline) is a natural material widely used in the food and pharmaceutical industries. Its amphoteric properties endow it with a compatibility toward lipids and water-soluble compounds, and is therefore useful for emulsifying fatty substances. In this connection it is used in manufacturing liposomes, or dispersions of lipid-soluble materials as droplets in water.

We find that this property seems to significantly enhance the ability of the hydrophobic growth factors present in DBM to exert their functions, to stabilize such molecules, and to delay their biodegradation. It also provides a very suitable carrier which enables the user to apply the DBM at sites in the body where it is desirable that it should be retained, such as sites of fractures or bony defects.

Such mixtures, which have a putty or visco-fluid consistency allow the DBM particles to remain in place long enough for them to release their bioactive principles at the site of action. It is well established that in the absence of suitable carriers the BMPs are rapidly carried away by body fluids and are therefore useless.

The composition of the present invention is perfectly suited for the purpose of generating bone. The calcium ions released from the calcium carbonate and other calcium salt further delay the solubilization process by forming insoluble calcium salts with the available organic phosphate present in a lecithin molecule.

Addition of antioxidants, such as vitamin E (tocopherol) and vitamin C (ascorbic acid or ascorbic acid derivatives) act as adjuvants and protect lecithin from oxidation. This is particularly useful as it relates to the process of sterilization of the lipid fraction using gamma radiation or electron beam radiation, which can generate free radicals which can otherwise destabilize the molecular structure of lecithin by oxidation.

Compositions according to the present invention can be prepared either in a solid (putty) form or in a liquid injectable form.

In one preferred embodiment in which the composition is a liquid putty for injection, the composition is suitable for injection through a large gauge needle from a syringe. In this preferred embodiment, DBM (30–40% w/w) was mixed with a lecithin preparation containing sufficient corn oil to allow the mixture to flow. In order to prevent the particles from settling, the consistency was enhanced (made less fluid) by the addition of palmitic acid (hexadecanoic acid). Usually a ratio of 1:5, that is approximately 20% of palmitic acid, melted by heating prior to mixing sufficed to generate a flowable suspension.

In another preferred embodiment, the putty is more hydrophilic and therefore easier to blend with the liquid blood-containing milieu at the site of application. The composition had a lipid fraction that had a lecithin:triglyceride ratio of 20:80 with 40% of demineralized bone matrix (DBM). To this putty preparation, 4% w/w of hydroxypropyl methylcellulose (Methocel) is added along with a small volume of water in the following ratios: 1 g of putty (containing DBM and the lipid fraction), 40 mg of hydroxypropyl methylcellulose, and 0.2 ml of water. The mixture holds well, is cohesive at 37° C., and remains as such when placed in saline at 37°.

The use of hydroxypropyl methylcellulose or similar hydrophilic polymers and their ability to swell in water and remain cohesive at 37° C. imparts an ability to the putty to interact more efficiently with blood, bone chips, or fragments which are present at the site of application, or when purposely mixed with small bony fragments to augment its volume and biocompatibility.

EXAMPLES

Example 1

Lecithin Enhances the Osteoinductivity of DBM

Introduction

Demineralized bone matrix (DBM), an osteoinductive bone graft material, is widely used for a variety of bone grafting applications. It is used alone or mixed with carriers to form gels, putties and sheets (M. R. Urist, *Science* 150: 893 (1965); E. R. Maddox et al., *Tissue Engineer.* 6: 441–448 (2000). Lecithin is a phospholipid present in cell membranes, and found in significant amounts in the bone calcification front (R. R. Wuthier, *Calcif. Tissue Res.* 19: 197–210 (1975)). The work reported in this Example examined the importance of lipids in the osteoinductive phenomenon. It also assessed the osteoinductive potential of a putty-like grafting material consisting of lecithin and DBM. In order to separate the osteoinductivity from any osteoconductive effects; the test materials were implanted ectopically (subcutaneously and intramuscularly), as well as adjacent to the cranial bone of rats.

Materials and Methods

Materials and Reagents: Lecithin (Phospholipon 90G, American Lecithin Company, Oxford, Conn.), is a purified phosphatidylcholine obtained from soybean.

Preparation of DBM/lecithin Conjugate: Fresh bones were procured from 180–220 g Fisher 344 rats. The cortical shafts were cleaned with several rinses of phosphate buffered saline (PBS), and soaked in ethanol to partially remove lipids and cellular debris. After freeze-drying, they were further ground into particle sizes of 100–500 $\mu$M, and decalcified with 0.6 N HCl/1% Triton X-100. For complete delipidation, particles were further soaked in 1:1 chloroform-methanol at room temperature for 12 hours. The DBM generated by such a process was designated as dDBM. Human DBM (Allosource, Denver, Colorado) was also tested; however, it was subjected to this delipidation process. Rat or human DBM was blended with lecithin to generate pastes of various concentrations (DBM concentrations from 20% to 80%). Composites were packed into gelatin capsules (No. 3, Eli Lilly, Ind.) for implantation.

Animal Implantation: Twenty-seven Fisher 344 rats and 12 athymic homozygous rnu/rnu (nude) rats were anesthetized and implants placed subcutaneously (SQ), intramuscularly, and subcutaneously adjacent to their cranial bones. Each animal received either four subcutaneous implants or two intramuscular implants. Implants were recovered 28 days postoperatively, fixed, decalcified, embedded and stained with hematoxylin-eosin (H & E) and Alcian Blue.

Alkaline Phosphatase Assay: Alkaline phosphatase activity was determined as previously described (M. E. Nimni et al., *Calcif. Tissue Int.* 37: 617 (1985)).

Results and Discussion

Properties of the DBM/Lecithin Composite: Lecithin mixed with the DBM particles gave rise to a composite with ointment-like consistency. It improved the handling properties of DBM which could be easily molded and fitted into irregularly shaped defects. The composite was insoluble in water and blood. When incubated at 37° C., the lecithin containing formulations maintained a solid state and did not liquify. The lecithin appeared to resorb within 7–14 days.

Endochondral and Intramembranous Bone Formation Using Human DBM/lecithin Composite: Endochondral bone formation was observed in the DBM/lecithin implants placed in the anterior abdominal wall musculature or subcutaneously for 28 days. New bone formation, characterized by bone matrix with osteocytes, is shown bridging DBM particles together in the implants (FIG. 1). FIG. 1 shows new bone formation in the DBM/composite after 28 days implantation: (a) subcutaneously; and (b) intramuscularly. The bridging of bone particles together generated tighter spaces within the implants that become hematopoietic marrow spaces. The devitalized DBM particles were clearly identified as amorphous stained material with empty osteocytic lacunae. Above the cranial bone there was a marked stimulation of new bone formation beyond the confines of the cranial structure.

Figure 2:
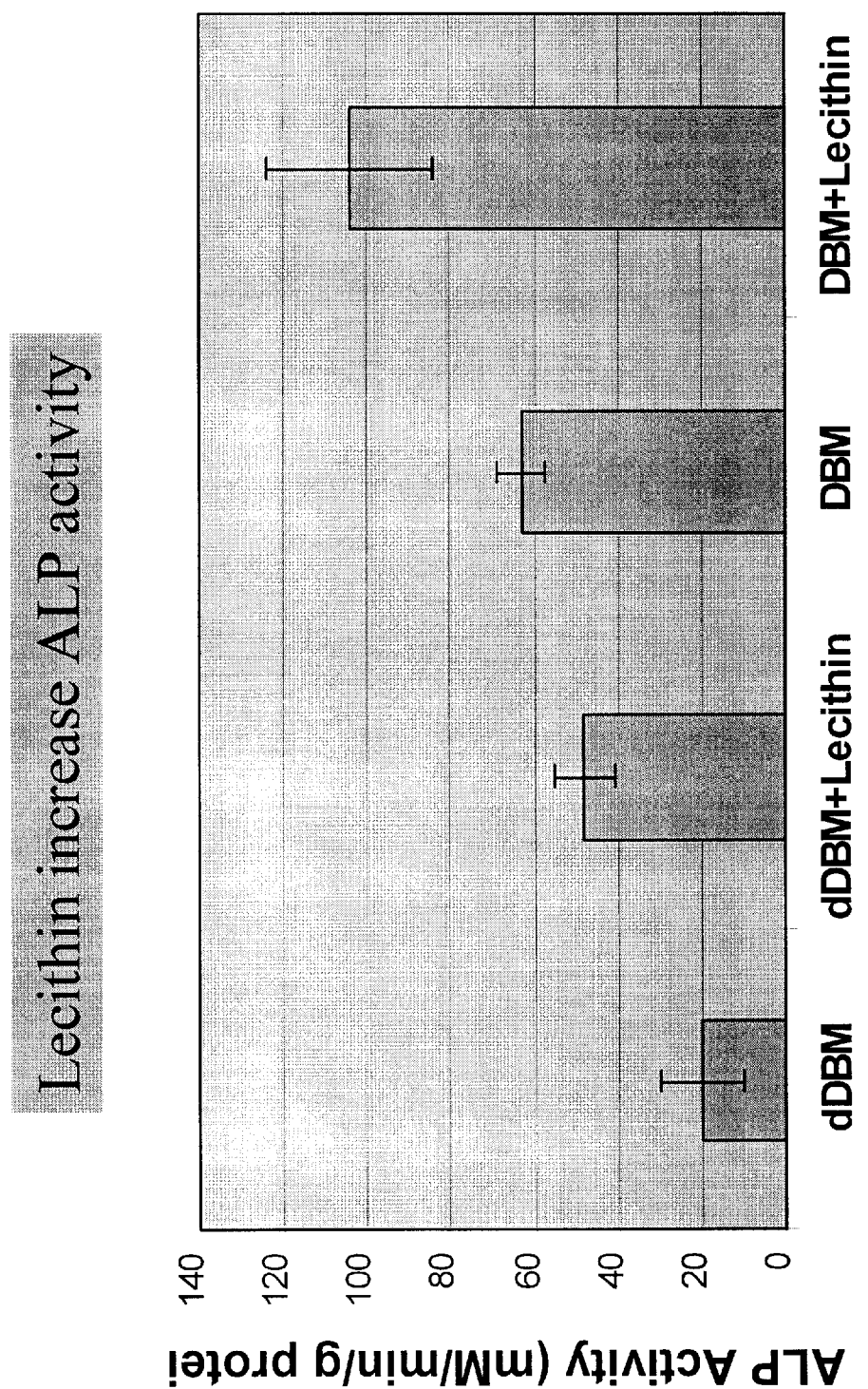
FIG. 2 is a graph showing the alkaline phosphatase (AP) activity (in mM/min/g protein) in 28-day postoperative explants with dDBM, dDBM/lecithin, DBM, and DBM/lecithin.

Lecithin Enhances Bone Formation: Delipidizing with chloroform/methanol decreased bone formation compared to standard DBM containing lipids, but when phospholipids in the form of lecithin were added back, bone formation rates were significantly enhanced, above the levels stimulated by DBM alone. The histological results were always confirmed by alkaline phosphatase analysis of the explants (FIG. 2). FIG. 2 is a graph showing the alkaline phosphatase (AP) activity (in mM/min/g protein) in 28-day postoperative explants with dDBM, dDBM/lecithin, DBM, and DBM/lecithin.

Implantation of the composite superperiosteally in the cranial region caused further marked bone deposition.

Discussion

Lecithin is a relatively stable phospholipid present in significant amounts in the calcification front. It does not readily dissolve in water, disperse or emulsify. Composites containing DBM and lecithin appear to be practical for filling osseous defects particularly when there is concern of implant washout or migration. Recently, Urist (M. R. Urist et al., *Connect. Tissue Res*36: 9–20 (1997)) found that endogenous lipids are closely associated with BMP and facilitated heterotopic bone formation. If completely delipidized with chloroform/methanol during the process of preparation, the rate of ectopic bone formation by demineralized bone matrix was decreased by 80%. In the study reported in this Example, when lecithin was added back to delipidized DBM, obtained from rats or from a human bone bank (which includes a partial delipidizing step), bone formation and the closely correlated alkaline phosphatase activities increased.

In conclusion, lecithin blended with DBM not only provides better handling properties, but also has the ability to enhance the osteoinductivity of DBM.

ADVANTAGES OF THE INVENTION

Compositions according to the present invention deliver a biologically active product to animals or humans which can enhance bone formation in sites where bone is lost, deficient, or present in sub-optimal amounts. This composition generates a suitable moldable vehicle for retaining the active principles at the site of bone repair. It is compatible with other treatments to enhance bone growth or regeneration and is well tolerated by the organism to which it is administered. The composition can be prepared in a number of different physical forms depending on the need and the proposed route of administration. The use of lecithin not only provides better handling properties, but also enhances the osteoinductivity of DBM.

While the specification describes particular embodiments of the present invention, those of ordinary skill can devise variations of the present invention without departing from the inventive concept.

I claim:

1. A demineralized bone putty composition comprising:
    (a) demineralized bone matrix (DBM); and
    (b) a lipid fraction selected from the group consisting of lecithin and a mixture of lecithin and triglycerides containing unsaturated fatty acids;
        such that the putty composition is moldable, biocompatible, slowly resorbable, insoluble in tissue fluids, and non-extrudable.

2. The composition of claim 1 wherein the composition comprises from about 20% to about 80% of DBM and from about 80% to about 20% of the lipid fraction.

3. The composition of claim 2 wherein the composition comprises about 30–40% of DBM and about 60% of the lipid fraction.

4. The composition of claim 3 wherein the composition comprises about 35–40% of DBM.

5. The composition of claim 1 wherein the lipid fraction comprises lecithin.

6. The composition of claim 1 wherein the lipid fraction comprises a mixture of lecithin and triglycerides containing unsaturated fatty acids.

7. The composition of claim 6 wherein the mixture of lecithin and triglycerides containing unsaturated fatty acids is about a 1:1 mixture.

8. The composition of claim 6 wherein the mixture of lecithin and triglycerides containing unsaturated fatty acids is about a 64:36 mixture.

9. The composition of claim 6 wherein the unsaturated fatty acids are from corn oil.

10. The composition of claim 9 wherein the ratio of lecithin and unsaturated fatty acids from corn oil is about 20:80.

11. The composition of claim 9 wherein the ratio of lecithin and unsaturated fatty acids from corn oil is about 40:60.

12. The composition of claim 9 wherein the ratio of lecithin and unsaturated fatty acids from corn oil is about 35:65.

13. The composition of claim 1 wherein the composition further comprises a calcium salt.

14. The composition of claim 13 wherein the proportion of the calcium salt is about 0.1% to about 2%.

15. The composition of claim 14 wherein the proportion of the calcium salt is from about 0.5% to about 2%.

16. The composition of claim 13 wherein the calcium salt is selected from the group consisting of $CaCO_3$ and $Ca_3(PO_4)_2$.

17. The composition of claim 16 wherein the calcium salt is $CaCO_3$.

18. The composition of claim 16 wherein the calcium salt is $Ca_3(PO_4)_2$.

19. The composition of claim 1 wherein the composition further comprises at least one antioxidant selected from the group consisting of Vitamin E and Vitamin C.

20. The composition of claim 19 wherein the antioxidant is Vitamin E.

21. The composition of claim 19 wherein the Vitamin E is tocopherol.

22. The composition of claim 20 wherein the Vitamin E comprises from about 0.01% to about 1.0% of the composition.

23. The composition of claim 22 wherein the Vitamin E comprises about 0.1% of the composition.

24. The composition of claim 19 wherein the antioxidant is Vitamin C.

25. The composition of claim 24 wherein the Vitamin C comprises from about 0.01% to about 2.0% of the composition.

26. The composition of claim 25 wherein the Vitamin C comprises from about 0.1% to about 0.5% of the composition.

27. The composition of claim 26 wherein the Vitamin C comprises about 0.2% of the composition.

28. The composition of claim 1 wherein the composition further comprises at least one ingredient selected from the group consisting of methylcellulose and hydroxypropyl methylcellulose.

29. The composition of claim 28 wherein the ingredient is methylcellulose.

30. The composition of claim 28 wherein the ingredient is hydroxypropyl methylcellulose.

31. The composition of claim 30 wherein the lipid fraction comprises a mixture of lecithin and triglycerides containing unsaturated fatty acids, the ratio of lecithin to triglycerides containing unsaturated fatty acids is about 20:80, the composition comprises about 40% of DBM, and the composition comprises about 4.0% of hydroxypropyl methylcellulose.

32. The composition of claim 1 wherein the lipid fraction is sterilized by radiation.

33. The composition of claim 1 wherein the phospholipids are liquid at room temperature.

34. The composition of claim 1 wherein the phospholipids are solid at room temperature.

35. The composition of claim 1 wherein the DBM is human DBM.

36. The composition of claim 1 wherein the DBM is rat DBM.

37. The composition of claim 1 wherein the DBM is DBM isolated from an animal species selected from the group consisting of cow, horse, pig, dog, cat, and sheep, or another socially or economically important animal species.

38. The composition of claim 1 wherein the DBM is delipidated.

39. The composition of claim 38 wherein the delipidation is performed by treatment with a mixture of chloroform and methanol.

40. The composition of claim 1 wherein the lipid fraction further contains a long-chain saturated fatty acid.

41. The composition of claim 40 wherein the long-chain saturated fatty acid is palmitic acid.

* * * * *